(12) United States Patent
Tietze

(10) Patent No.: US 11,977,016 B2
(45) Date of Patent: May 7, 2024

(54) HIGHLY SELECTIVE AND ULTRASENSITIVE METAL ION SENSOR

(71) Applicant: AMiLion Technology AB, Gothenburg (SE)

(72) Inventor: Alesia Tietze, Mölndal (SE)

(73) Assignee: AMiLion Technology AB, Gothenburg (SE)

(*) Notice: Subject to any disclaimer, the term of this patent is extended or adjusted under 35 U.S.C. 154(b) by 485 days.

(21) Appl. No.: 17/421,837

(22) PCT Filed: Jan. 9, 2020

(86) PCT No.: PCT/EP2020/050461
§ 371 (c)(1),
(2) Date: Jul. 9, 2021

(87) PCT Pub. No.: WO2020/144294
PCT Pub. Date: Jul. 16, 2020

(65) Prior Publication Data
US 2022/0099548 A1    Mar. 31, 2022

(30) Foreign Application Priority Data
Jan. 10, 2019   (EP) .................................... 19151227

(51) Int. Cl.
*G01N 15/06*   (2006.01)
(52) U.S. Cl.
CPC ..... *G01N 15/06* (2013.01); *G01N 2015/0687* (2013.01); *G01N 2015/0693* (2013.01)
(58) Field of Classification Search
CPC ........... G01N 15/06; G01N 2015/0687; G01N 2015/0693
See application file for complete search history.

(56) References Cited

U.S. PATENT DOCUMENTS 7,041,642 B1\* 5/2006 Desjardins ....... C07K 14/57536
435/7.1
2013/0306485 A1\* 11/2013 Varghese ........... G01N 33/6812
205/171

FOREIGN PATENT DOCUMENTS

WO    WO-2020144294 A1 \*  7/2020   ........... C07K 5/0202

OTHER PUBLICATIONS

Martinez-Manez et al., "Mimicking Tricks From Nature With Sensory Organic-Inorganic Hybrid Materials", Journal of Materials Chemistry, vol. 21, No. 34, 2011, pp. 12588-12604.

(Continued)

*Primary Examiner* — Jamel E Williams
(74) *Attorney, Agent, or Firm* — Kilpatrick Townsend & Stockton LLP

(57) ABSTRACT

The present application is directed to a sensor for detection and/or concentration determination of metal ions in a fluid comprising a complexing agent suitable for binding the metal ions to be detected, detection means and a linker moiety, wherein the detection means comprises a polymer membrane with nanopores. The sensor according to the present application can be used for fast, highly selective and ultrasensitive detection of metal ions in a fluid, in particular of $Cu^{2+}$ ions. With such a sensor a qualitative and/or quantitative detection of metal ions can be achieved, which can be useful in the diagnosis and/or monitoring of diseases linked to abnormal metal ion concentrations such as for example Alzheimer's disease.

22 Claims, 11 Drawing Sheets

(56) References Cited

OTHER PUBLICATIONS

Mayne et al., "A Tunable Nanopore Sensor for the Detection of Metal Ions Using Translocation Velocity and Biphasic Pulses", Nanoscale, vol. 8, No. 45, Oct. 27, 2016, pp. 19139-19147.
Meng et al., "Synthesis, Functionalization and Application of Stimuli-Responsive Polymer Porous Membranes", Current Organic Chemistry, vol. 22, No. 8, 2018, pp. 737-749.
International Application No. PCT/EP2020/050461, International Search Report and Written Opinion, date Apr. 9, 2020, 11 pages.
Politi et al., "Reversible Sensing of Heavy Metal Ions Using Lysine Modified Oligopeptides on Porous Silicon and Gold", Sensors and Actuators B: Chemical, vol. 244, Jun. 2017, pp. 142-150.
Torrado et al., "Exploiting Polypeptide Motifs for the Design of Selective Cu(II) Ion Chemosensors", Journal of the American Chemical Society, vol. 120, No. 3, 1998, pp. 609-610.
Wang et al., "Nanopore Detection of Copper Ions Using a Polyhistidine Probe", Biosensors and Bioelectronics, vol. 53, Mar. 15, 2014, pp. 453-458.
Wende et al., "Copper Complexes of N-Donor Ligands as Artificial Nucleases", European Journal of Inorganic Chemistry, vol. 2014, No. 16, Jun. 2014, pp. 2597-2612.
Yadavi et al., "A Novel Fe3+ Ions Chemosensor by Covalent Coupling Fluorene Onto the Mono, Di- and Tri-Ammonium Functionalized Nanoporous Silica Type SBA-15", Applied Surface Science, vol. 279, Aug. 15, 2013, pp. 121-128.
Hirayama et al., "Near-infrared fluorescent sensor for in vivo copper imaging in a murine Wilson disease model", Proc Nat Acad Sci USA, Feb. 14, 2012, 109, pp. 2228-2233.
Torrado et al., "Exploiting Polypeptide Motifs for the Design of Selective Cu(II) Ion Chemosensors", J Am Chem Soc 1998, 120, pp. 609-610.
Papp et al., "Ion-Selective Electrodes Based on Hydrophilic Ionophore-Modified Nanopores", Angewandte Chem Int Ed Engl , Apr. 16, 2018, 57, pp. 4752-4755.
Sokolowska et al., "Short peptides are not reliable models of thermodynamic and kinetic properties of the N-terminal metal binding site in serum albumin", Eur J Biochem 2002, 269, pp. 1323-1331.
Squitti et al., "Meta-Analysis of Serum Non-Ceruloplasmin Copper In Alzheimer's Disease", J Alzheimers Dis 2014, 38, pp. 809-822.
Georgopoulos et al., "Environmental copper: its dynamics and human exposure issues", Journal of Toxicol Environ Health B Crit Rev Oct. 2001, pp. 1-216.
Kim et al., "Mechanisms for copper acquisition, distribution and regulation", Nature Chemical Biology, vol. 4, No. 3, Mar. 2008, pp. 176-185.
Goldsmith et al., "Particulate Air Pollution and Asthma: A Review of Epidemiological and Biological Studies", Rev Environ Health, vol. 14, No. 3, 1999, pp. 121-134.
Hong et al., "Corrosion and Leaching of Copper Tubing Exposed to Chlorinated Drinking Water", Water, Air and Soil Pollution, 108, 1998, 457-471.
Brown et al., "Biological inorganic and bioinorganic chemistry of neurodegeneration based on prion and Alzheimer diseases", 4. Dalton Trans 2004, 1907-1917.
Harford et al., "Amino Terminal Cu(II)- and Ni(II)-Binding (ATCUN) Motif of Proteins and Peptides: Metal Binding, DNA Cleavage, and Other Properties", 5. Accounts of Chemical Research 1997, 30, 123-130.
Situ et al., "Naked-eye detection of copper(II) ions by a "clickable" fluorescentsensor", Sensors and Actuators B-Chemical, Mar. 2017, 240, pp. 560-565.
Ding et al., "Label-free ultrasensitive colorimetric detection of copper(II) ions utilizing polyaniline/polyamide-6 nano-fiber/net sensor strips", Journal of Materials Chemistry 21, 2011, pp. 13345-13353.
Torrisi et al., "Ion and neutral emission from pulsed laser irradiation of metals", Nucl Instrum Methods Phys Res, Sect. B, 184, 2001, pp. 327-336.
Squitti et al.,"Copper dyshomeostasis in Wilson disease and Alzheimer's disease as shown by serum and urine copper Indicators", Journal of Trace Elem Med Biol, Jan. 45, 2018, pp. 181-188.

* cited by examiner

HIGHLY SELECTIVE AND ULTRASENSITIVE METAL ION SENSOR

The present application is directed to a sensor for detection and/or concentration determination of metal ions in a fluid, the use of such a sensor in the diagnosis and/or monitoring of diseases and a method for the qualitative and quantitative detection of metal ions in a fluid sample. In particular, the sensor of the present application may be used for selectively detecting $Cu^{2+}$ ions in a fluid and for concentration determination of $Cu^{2+}$ ions in a fluid.

Detection and concentration determination of biologically and environmentally significant metal ions has become of great interest in the field of chemical sensors in recent years. Fluorescence as detection method plays an important role in the field of chemical sensors, in particular due to its straight-forward application and sensitive detection limit. Selectivity and sensitivity for particular metal ions is usually achieved by using suitable complexing agents linked to fluorophores such as rhodamin, fluorescein, pyrene, anthracen, naphtalimide and cumarin. Biologically and environmentally interesting target ions are for example $C^{2+}$, $Ni^{2+}$, $Zn^{2+}$, $Hg^{2+}$, $Pb^{2+}$ and $Cd^{2+}$.

For example, copper is an essential trace element that is inevitable in biological systems and can be found in many enzymes such as amine oxidases and ferroxidases but is also required for infant growth, the ion metabolism and brain development in human organisms (*Nat Chem Blot* 2008, 4, 176-185; *J Toxicol Environ Health B Crit Rev* 2001, 4, 341-394). Copper is also widely used in agricultural systems and therefore belongs to a major metal pollutant in our environment (*Rev Environ Health* 1999, 14, 231-238). The contamination of ecosystems such as rivers, lakes, soil and groundwater with copper causes increased accumulation (*Chem Soc Rev* 2017, 46, 7105-7123).

There are also diseases linked to an abnormal copper concentration and/or dysregulated copper metabolism in humans such as Wilson's disease, Menke's disease and Alzheimer's disease (AD) (*Water, Air and Soil Pollution* 1998, 108, 457-471). Dysregulation of copper homeostasis causes neurodegenerative diseases, which led to a rising interest in the investigation of the connection between copper and AD (*Dalton Trans* 2004, 1907-1917).

In recent years first steps have been taken towards the development of screening methods and sensors for the determination of copper for early AD diagnostics. For example. Hirayama et al. (*Proc Nat Aced Sci USA* 2012, 109, 2228-2233) developed a copper-imaging sensor inside of living cells with a sensitive fluorescence turn-on response to $Cu^{1+}$. However, this method depends on live-cell imaging after digestion of the fluorescent dye and thus the detection method itself and its implementation is tied to an extensive set-up. Squitti et al. (*J Alzheimers Dis* 2014, 38, 809-822) designed a method using fluorescence to detect non-CP $Cu^{2+}$ i.e. detection of free $Cu^{2+}$ that is not bound to ceruloplasmin distributed in the serum. However, also this method requires an extensive two-step experimental set-up with a size exclusion solid-phase extraction separating non-CP $Cu^{2+}$ from protein-bound copper followed by a fluorescent method, which also requires a lengthy time period to obtain results.

It is known that peptides in proteins can display extraordinary and ultrasensitive key-lock behavior towards targets. Copper-binding peptides in nature are albumin (bovine serum albumin (BSA), human serum albumin (HSA), rabbit serum albumin (RSA)), neuromedin C and K, human sperm protamine P2a and histidines (*Accounts of Chemical Research* 1997, 30, 123-130). Imperiali et al. (*J Am Chem Soc* 1998, 120, 609-610) reported polypeptide motifs for the design of selective Cu(II) ion chemosensors. Papp et al. (*Angewandte Chem Int Ed Engl* 2018, 57, 4752-4755) were able to attach the amino terminal Cu(II) and Ni(II)-binding (ATCUN) motif (Gly-Gly-His) on track-etched polycarbonate membranes. A copper-sensing system that can be evaluated by naked eye detection with a detection limit of 0.5 µM using a "turn-on" fluorescence strategy is reported by Situ et al. (*Sensors and Actuators B-Chemical* 2017, 240, 560-565), however, with the disadvantage that the detection method involves several reaction steps. Further, naked eye detectable sensor systems were constructed by Ding et al. (*Journal of Materials Chemistry* 2011, 21, 13345-13353) presenting a colorimetric detection of copper using sensor strips at a detection limit of 5 nM.

Due to the ongoing need for highly sensitive and selective detection methods for metal ions it is an object of the present application to provide a sensor allowing a fast and easy-to-handle, but highly sensitive and selective qualitative and quantitative detection of metal ions in a fluid, in particular for detecting metal ion concentrations in body fluids and in environmental samples in low concentrations.

According to the invention, this problem has been solved by providing a sensor for detection and/or concentration determination of metal ions in a fluid comprising a complexing agent suitable for binding the metal ions to be detected, detection means and a linker moiety, wherein the detection means comprises a polymer membrane with nanopores. The sensor according to the present application can be used for fast, highly selective and ultrasensitive detection of metal ions in a fluid. With said sensor a qualitative and/or quantitative detection of metal ions can be obtained, in particular by measuring the change in the current-voltage characteristics and/or by measuring the change in fluorescence intensity. It was in particular found that the combination of a complexing agent attached to a polymer membrane allows for ultrasensitive, quantitative detection of metal ions, in particular of $Cu^{2+}$ ions, as low as the femtomolar range.

In one embodiment, the qualitative and quantitative detection of metal ions is performed by observing a change in the current-voltage characteristics, which allows the detection of metal ion concentrations in a fluid in the femtomolar range, i.e. as low as 1 fM. M refers to the molar concentration mol per liter (mol/L). In a further embodiment, the qualitative and quantitative detection of metal ions may be performed by observing a change in the fluorescence intensity. Such a detection method does not require an extensive experimental set-up. In fact, with the sensor of the present application detection of metal ions is possible on-site and in real time. For example, simply a test strip comprising the sensor according to the present application with a fluorophore attached to the complexing agent and a fluorescence-light source may be required.

Generally, sensors are devices for detecting particular analytes, in the case of the present invention the analytes are metal ions such as $Fe^{2+}/Fe^{3+}$, $Co^{2+}$, $Cu^{2+}$, $Ni^{2+}$, $Zn^{2+}$, $Hg^{2+}$, $Pb^{2+}$, $Cd^{2+}$, $Ag/Ag^+$ and $Au/Au^+$, in particular $Cu^{2+}$. The sensor provides the information regarding the analyte usually in the form of a measurable physical signal correlated with the presence and/or concentration of the analyte.

The sensor of the present application comprises a complexing agent suitable for binding the metal ions to be detected. Preferably, the complexing agent is a peptide comprising 2-6 amino acids, modified amino acids and/or amino acid mimics. The complexing agent may thus also be referred to as peptide complexing agent. The complexing agent acts as a chelating ligand and forms a chelating complex with the metal ion to be detected providing a chelating complex. Depending on the metal ion to be detected, the complexing agent is selected.

The amino acids of the peptide are selected from the group consisting of standard amino acids, unusual amino acids, non-proteinogenic amino acids or amino acid mimics and modified amino acids. Examples for standard L-amino acids are glycine (Gly), alanine (Ala), valine (Val), leucine (Leu), methionine (Met), isoleucine (Ile), serine (Ser), threonine (Thr), cysteine (Cys), proline (Pro), asparagine (Asn), glutamine (Gln), phenylalanine (Phe), tyrosine (Tyr), tryptophan (Trp), lysine (Lys), arginine (Arg), histidine (His), aspartic acid (Asp) and glutamate (Glu). Preferred standard amino acids according to the present invention are histidine (His), alanine (Ala) or aspartic acid (Asp). Examples for unusual amino acids are 4-hydroxyproline, 5-hydroxylysine, 6-N-methyllysine, γ-carboxyglutamate, desmosine, selenocysteine, ornithine and citroline. Non-proteinogenic amino acids or amino acid mimics are amino acids which are not incorporated in proteins during translation. However, they may be incorporated into an amino acid scaffold by chemical synthesis methods. Non-proteinogenic amino acids or amino acid mimics according to the present application may be for example 2,3-diaminopropionic acid (DAP) and β-alanine. 2,3-diaminopropionic acid (DAP) may be L-2,3-diaminopropionic acid, D-2,3-diaminopropionic acid or a mixtures of L- and D-DAP. L-2,3-diaminopropionic acid is preferred. A modified amino acid comprises standard or unusual amino acids, which may be for example methylated, acetylated or its diastereomeric D, cis/trans and isosteric form.

In a preferred embodiment, the sensor of the present invention is for detection and/or concentration determination of $Cu^{2+}$ ions and the complexing agent is a copper-binding motif such as the ATCUN-binding motif or an ATCUN-like binding motif functioning as an ATCUN-binding motif. Preferably, the copper-binding motif comprises four electron-donor moieties, in particular at least three nitrogen atoms with the fourth electron donor being nitrogen, sulfur or oxygen. The $Cu^{2+}$ ion then forms a square planar complex with the copper-binding motif comprising at least three nitrogen atoms. Examples for such copper-binding motifs are ATCUN-binding motifs or ATCUN-like binding motifs to be used as complexing agents in the sensor of the present application as shown in FIG. 2e). The ATCUN-binding motifs may be linear or cyclic peptides such as the linear tri-peptide Gly-Gly-His. Preferably, the complexing agent is a copper-binding motif peptide such as the tri-peptide 2,3-diaminopropionic acid (DAP)-βAla-X, wherein X is an amino acid or a modified amino acid, in particular wherein X is histidine (His), alanine (Ala) or aspartic acid (Asp). In particular, the sensor of the present application comprises as complexing agent the peptide compound DAP-βAla-His, DAP-βAla-Asp, or DAP-βAla-Ala, in particular for detection of $Cu^{2+}$ ions.

The sensor according to the present application comprises a polymer membrane with nanopores as means for detection. Detection means or means for detection are able to produce a measurable, physical signal.

The polymer membrane, foil or sheet with nanopores is a functionalized polymer membrane, foil or sheet with nanopores, in particular an ion-track etched polymer membrane, foil or sheet with nanopores, even more preferably an ion-track etched polyethylene terephthalate (PET)-membrane, foil or sheet with nanopores. The functionalized polymer membrane with nanopores is a polymer membrane with functional groups such as carboxylate and/or amino groups on the surface of the membrane and on the surface of the nanopores. The polymer membrane may also be made of polycarbonate (PC) or may be made of any polymer material which can be chemically functionalized. Preferably, the polymer membrane has a thickness of 1 to 30 µm, preferably 10-20 µm, and more preferably 11-15 µm. An example for such a PC and PET polymer membrane or foil are ipPORE™ track-etched membranes by it4ip®.

The nanopores may have any shape, but preferably have a conical or a cylindrical shape. Most preferably, the nanopores are conical. The conically shaped nanopores preferably have small openings of about 2-10 nm in diameter, preferably 4-6 nm in diameter, and big openings of 200-500 nm in diameter, preferably 300-400 nm in diameter. The length of the pores is between 10-20 µm, preferably 12-15 µm. The length corresponds to the thickness of the polymer membrane. In a preferred embodiment, the conically shaped nanopores have a small opening of about 5 nm in diameter, a big opening of about 300 nm in diameter and a length of about 12 µm. The cylindrical nanopores have openings of 50-500 nm in diameter, preferably 100-400 nm in diameter and a length of between 10-20 µm, preferably 12-15 µm. The length corresponds to the thickness of the polymer membrane.

The polymer membrane, foil or sheet preferably contains about 1 to $10^7$ nanopores per $cm^2$, preferably about $10^3$ to $10^5$ nanopores per $cm^2$, more preferably about $10^4$ nanopores per $cm^2$. Ion-track etched polymer membranes, foils or sheets with conical nanopores can be obtained by the known procedure of asymmetric chemical etching of the latent ion track as described in *Nucl Instrum Methods Phys Res, Sect. B* 2001, 184, 337-346. After heavy ion irradiation and subsequent chemical etching process of the polymer membranes, foils or sheets, carboxylic acid groups are generated on the surface of the polymer membrane, foil or sheet, in particular on the nanopore surface of the ion-track etched polymer membrane, foil or sheet, which can be used for covalent attachment of functional molecules containing for example a primary amine.

The detection means according to the present application may further comprise a fluorophore, for example commercially available fluorophores such as 5(6)-carboxyfluorescein, DyLight Fluor, Alexa Fluor or cyanine dyes. A preferred fluorophore in the sensor of the present application is 5(6)-carboxyfluorescein. The fluorophore may be attached to the complexing agent via the N-terminus of an amino acid of the peptide.

The quenching or amount of quenching or increase or amount of increase of the fluorescence intensity indicates the presence of metal ions in the fluid, i.e. binding of metal ions to the complexing agent of the sensor. This change in fluorescence intensity can be used to calculate the metal ion concentration in the fluid as the amount of quenching or decrease is proportional to the metal ion concentration in the fluid. The "on-off" characteristics of such a detection method using the sensor of the present application comprising a copper binding motif as complexing agent in the detection of $Cu^{2+}$ ions is shown in FIG. 1.

The inventors of the present invention found also that a sensor comprising a polymer membrane with nanopores allows for a highly reliable and highly sensitive measurement of metal ions when using as further detection means a fluorophore attached to the peptide complexing agent. This is because the fluorescence intensity is increased inside the nanopores of the polymer membrane. This increase results from the attachment of the fluorescent labeled complexing agent molecules to the nanopore surface inside the pore. The complexing agent molecules with the fluorophore i.e. the fluorescent labeled complexing agent molecules are stacked inside the pores parallel to the surface of the membrane and perpendicular to the direction of the detection. Thus, the fluorescence intensity of the fluorescent labeled complexing agent molecules superimposed on each other in the direction of measurement is accumulated over the length of the nanopore resulting in a much higher and better detectable signal compared to a monolayer of fluorescent labeled complexing agents on a flat surface when viewed from the direction of detection.

In a preferred embodiment, the sensor of the present application comprises a polymer membrane with nanopores, in particular an ion-track etched PET membrane with nanopores and a fluorophore such as 5(6)-carboxyfluorescein as detection means. In a particularly preferred embodiment of the present application, the sensor comprises 5(6)-carboxyfluorescein-DAP-βAla-His, 5(6)-carboxyfluorescein-DAP-βAla-Asp, or 5(6)-carboxyfluorescein-DAP-βAla-Ala as fluorescent labeled complexing agent, i.e. a complexing agent to which as further detection means a fluorophore is attached.

The sensor according to the present application further comprises a linker moiety, which is preferably bound to the polymer membrane with nanopores and to the complexing agent, i.e. is positioned between these two moieties. The linker moiety links the complexing agent to which preferably a fluorophore is attached to the polymer membrane with the nanopores and immobilizes the complexing agent preferably with the fluorophore on the surface of the polymer membrane with the nanopores. The linker moiety is for ensuring a spatial separation of the functional groups of the complexing agent such as a copper-binding motif and optionally the fluorophore to the polymer membrane, foil or sheet. Thereby an undesired interaction between the functional groups on the surface of the polymer membrane, foil or sheet and the complexing agent and optionally the fluorophore can be avoided.

Preferably, the linker moiety comprises polyethylene glycol (PEG) units, in particular 4 PEG units. The linker moiety preferably has the formula $R_1$—$[CH_2CH_2O]_a$—$R_2$, wherein subscript a is from 2 to 10, $R_1$ is —NH and $R_2$ is $CH_2CH_2COOH$ or $CH_2CH_2CCH_3$=O. In the formula $R_1$—$[CH_2CH_2O]_a$—$R_2$ a may be 2 to 8, 2 to 6, 2 to 4, 4 to 10, 4 to 8 or 4 to 6, more preferably a is 3, 4, 5 or 6 and most preferable a is 4. In a preferred embodiment the linker has the structure —HN—$[CH_2CH_2O]_4$—$CH_2CH_2COO(H)$— (FIG. 2(e)) referred to as linkerPEG$_4$ in the present invention. If the linker comprises a carboxy group $R_2$=COO(H)— coupling by means of said carboxy group to the polymer membrane, foil or sheet can be achieved. For example, the carboxy group of the linker may be coupled to an amino functional group on the surface of the polymer membrane via standard peptide coupling chemistry. The amino group $R_1$ allows coupling to the C-terminus of an amino acid of the peptide complexing agent, also by means of standard peptide coupling chemistry.

In one embodiment of the present application, a copper-binding motif as peptide complexing agent with a fluorophore may be attached by means of the linker moiety to the surface of the polymer membrane with nanopores, in particular to the ion-track etched polymer membrane, foil or sheet, in particular to the surface of the nanopores. Preferably, the complexing agent with or without the fluorophore is attached via the linker moiety to both the surface of the membrane and to the surface inside the nanopores. For example, binding of $Cu^{2+}$ ions to a copper-binding motif of the sensor according to the present invention changes the current-voltage characteristics of the polymer membrane, foil or sheet with the nanopores which can then be used for qualitative and quantitative detection of $Cu^{2+}$ ions in the fluid, allowing the detection of $Cu^{2+}$ ion concentrations as low as 1 fM.

In a preferred embodiment, the sensor according to the present application comprises the copper-binding motif DAP-βAla-X as complexing agent, detection means and a linker, wherein the detection means is a polymer membrane with nanopores, in particular an ion-track etched PET-membrane, foil or sheet with nanopores and a fluorophore, in particular 5(6)-carboxyfluorescein. The fluorophore is attached to the N-terminus of the DAP and the linker moiety is attached to the C-terminus of the amino acid or modified amino acid X. The copper-binding motif is attached via the linker moiety to the surface of the polymer membrane, foil or sheet, in particular to the surface of the nanopores.

The sensor according to the present application is used for detecting metal ions in a fluid, which fluid can be obtained from any source. The fluid may comprise a liquid, preferably an aqueous or water-based liquid, for example from environmental sources. The aqueous or water-based liquid may also be an emulsion. Examples for a liquid according to the present invention are drinking water and body fluids such as urine, whole blood, plasma, serum, extracellular interstitial fluid, lymph, bile, cerebrospinal liquid as well as gland secretion such as saliva or sweat, wherein urine is preferred. The aqueous or water-based liquid further may originate from water streams, puddles, lakes and seas. Prior to subjecting the fluid sample to the sensor of the present application, the sample lay be filtered, concentrated, centrifuged, chemically treated and the like.

In a preferred embodiment, the sensor according to the present application is able to selectively detect $Cu^{2+}$ ions in a fluid in the presence of $Ni^{2+}$ ions and/or $Zn^{2+}$ ions. Selective detection of $Cu^{2+}$ ions according to the present application means that in case no $Cu^{2+}$ ions are present in the fluid, but $Ni^{2+}$ ions and/or $Zn^{2+}$ ions are, no signal indicating the presence of the desired analyte $Cu^{2+}$ ions is generated by the detection means. For example, when using 5(6)-carboxyfluorescein as fluorophore, no quenching in fluorescence intensity would be observed. Further, the presence of $Ni^{2+}$ ions and/or $Zn^{2+}$ ions in addition to a particular concentration of $Cu^{2+}$ ions in the fluid does not change the signal of the detection means by more than ±5%, i.e. almost identical results are obtained for the $Cu^{2+}$ ion concentration in a solution containing $Ni^{2+}$ ions and/or $Zn^{2+}$ ions as for a solution containing $Cu^{2+}$ ions, but no $Ni^{2+}$ ions and/or $Zn^{2+}$ ions. In this embodiment, the complexing agent is preferably the copper-binding motif 2,3-diaminopropionic acid (DAP)-βAla-X, wherein X is an amino acid or a modified amino acid, in particular wherein X is histidine (His), alanine (Ala) or aspartic acid (Asp) and the fluorophore is attached thereto.

In one embodiment, the sensor according to the present application is for use in the diagnosis and/or monitoring of diseases, preferably of diseases linked to abnormal $Cu^{2+}$ ion (copper) concentrations and/or dysregulated $Cu^{2+}$ ion (copper) metabolism such as Alzheimer's disease, Wilson's disease and Menke's disease. $Cu^{2+}$ ion concentrations in terms of diagnosis and/or monitoring of diseases, in particular when determining the $Cu^{2+}$ ion concentration in urine refer to copper, i.e. $Cu^{2+}$ ions that is not bound to ceruloplasmin (non-CP Cu). Such copper may also be termed "free $Cu^{2+}$ ions" or "free $Cu^{2+}$ ions in solution".

The term "abnormal" in relation to $Cu^{2+}$ ion (copper) concentration according to the present application means that the $Cu^{2+}$ ion concentration in a body fluid is higher or lower compared to healthy individuals. Higher $Cu^{2+}$ ion concentration in a body fluid, far example urine, is observed in individuals having a particular disease such as Alzheimer's disease or Wilsons's disease. Lower $Cu^{2+}$ ion concentration in a body fluid is observed in individuals having a disorder correlated to copper deficiency such as Menke's disease. In healthy individuals the concentration of non-ceruloplasmin-bound $Cu^{2+}$ ((non-CP Cu) in urine is in a range of 40 to 50 nM calculated based on a $Cu^{2+}$ ion amount of about 4.82 µg/day in 1.5 to 2.0 L urine (*J Trace Elem Met Biol* 2018, 45, 181-188). Thus, a $Cu^{2+}$ ion concentration in urine above 40-50 nM, for example at least twice as high than in healthy individuals, i.e. above 80 or 90 nM, in particular in a range of 100 to 130 nM as is often the case for AD patients is considered an abnormal copper or $Cu^{2+}$ ion concentration.

In a preferred embodiment, the sensor according to the present application is for use in the diagnosis and/or monitoring of Alzheimer's disease (AD), Wilson's disease and Menke's disease. In a further preferred embodiment, the sensor according to the present application is for use in determining $Cu^{2+}$ ion concentration in the urine of individuals to diagnose and/or monitor diseases linked to abnormal $Cu^{2+}$ ion (copper) concentrations and/or dysregulated $Cu^{2+}$ ion (copper) metabolism, in particular Alzheimer's disease, Wilson's disease and Menke's disease. The use of the sensor of the present application is in particular for an ex vivo determination of $Cu^{2+}$ ion concentration in body fluids, preferably in the urine of individuals.

Alternatively, the sensor according to the present application may be for use in detecting metal ions and/or determining metal ion concentration in food products or fluids such as aqueous or water-based liquids, in particular in food/water control and/or environmental samples. Preferred metal ions in this regard are $Fe^{2+}/Fe^{3+}$, $Cu^{2+}$, $Ni^{2+}$, $Zn^{2+}$, $Hg^{2+}$, $Pb^{2+}$, $Cd^{2+}$, $Ag/Ag^+$ and $Au/Au^+$, in particular $Cu^{2+}$.

Particularly, the sensor according to the present application may be used for multiple measurements, i.e. the sensor allows a repeated measurement of metal ions or metal ion concentration.

The present application further discloses a method for the qualitative and quantitative detection of metal ions, in particular $Cu^{2+}$ ions in a fluid. In a first step the sensor is brought into contact with the fluid sample. This may be done for example by immersing a test strip with the immobilized sensor in the fluid sample or by mixing a solution of the sensor of the present application with the fluid sample or by dripping the fluid sample onto the sensor of the present application. In the next step, detection of metal ions and/or determining the metal ion concentration of the sample takes place. Depending on the detection means different parameters are used as basis for qualitative and/or quantitative detection of metal ions in the fluid sample. In case the sensor comprises a fluorophore as further detection means, in particular 5(6)-carboxyfluorescein, quenching of the fluorescence intensity upon contact of the sensor with the analyte metal ions is observed, i.e. a change in fluorescence intensity is measured. As can be seen in FIG. 3(*a*),(*b*) a linear decrease of fluorescence intensity of the sensor upon addition of $Cu^{2+}$ ions in water can be clearly observed showing more and more quenching of the fluorescence intensity with increasing $Cu^{2+}$ ion concentrations.

The method of the present invention may further comprise a step of adjusting the pH of the fluid sample, in particular prior to subjecting it to the sensor of the present invention. When detecting $Cu^{2+}$ ions the method comprises the step of adjusting the pH of the fluid sample to be analyzed to 5.0 to 8.5, preferably to a pH of 5.5. to 8.0, 6.0 to 7.3, 6.3 to 8.0 or 6.5 to 7.5 and most preferably to a pH of 6.5 to 7.0. By adjusting the pH of the fluid sample to be analyzed the selectivity of the sensor according to the present application towards $Cu^{2+}$ ions is ensured, in particular selectivity towards $Cu^{2+}$ ions over $Ni^{2+}$ and $Zn^{2+}$ ions. Setting the pH of the fluid sample to the claimed range, i.e. to a pH range of 5.0 to 8.5 leads to formation of a complex only between $Cu^{2+}$ ions and the complexing agent, i.e. the copper-binding motif of the sensor. The formation of $Ni^{2+}$- or $Zn^{2+}$-complexes at the claimed pH-range with the copper-binding motif of the sensor is insignificant. Adjusting the pH of the fluid may be done prior to bringing the sensor into contact with the fluid sample or at the same time when bringing the sensor into contact with the fluid sample.

Without being bound by theory, it is assumed that upon binding of the copper-binding motif such as DAP-βAla-His of the sensor to the $Cu^{2+}$ ions a square planar complex is formed having a d-d transition band at 537 nm (FIG. 2(*a*)). As can be seen in FIG. 2(*b*) of the present application Ni-complexation of the sensor according to the present application significantly starts at around >pH 7, which Ni-complex shows a transition band at 438 nm (FIG. 2(*a*)). Thus, adjusting the pH in relation to the pH-dependent formation of the $Cu^{2+}$- and $Ni^{2+}$-complex, taking into account up to which pH range the $Ni^{2+}$-complex is not formed, a highly selective detection method for $Cu^{2+}$ ions in a fluid is enabled.

Performing quantitative and/or qualitative detection of $Cu^{2+}$ ions with the sensor according to the present application in a fluid with a pH range of 5.0 to 8.5, preferably in a pH range of 5.5. to 8.0, 6.0 to 7.3, 6.3 to 8.0 or 6.5 to 7.5 and even more preferably at a pH range of 6.5 to 7.0 corresponding to $pH_{50}$ of the copper-sensor, i.e. the pH value at which 50% of the $Cu^{2+}$-complexes have been formed, allows for selective detection of $Cu^{2+}$ ions also in the presence of $Ni^{2+}$ ions in the fluid sample, since at the claimed pH range only insignificant or no complexation of $Ni^{2+}$ is present.

In one embodiment, the qualitative and quantitative detection of metal ions, in particular $Cu^{2+}$ ions in the fluid sample may be achieved by monitoring the change in the current-voltage (I-V) characteristics of the sensor according to the present invention. By measuring the changes in the current-voltage (I-V) characteristics of the sensor, a quantitative and qualitative detection of metal ions in a fluid sample is feasible. The detection of metal ion concentrations, in particular $Cu^{2+}$ ion concentrations in a fluid sample with metal ion concentrations as low as 1 fM can be done, in particular in a range from 1 fM to 30 mM, 1 fM to 20 mM, 1 nM to 10 mM, 1 nM to 5 mM, in particular in a range from 1 fM to 60 µM, 5 nM to 40 µM, 10 nM to 10 µM, 12 nM to 5 µM, 1 nM to 500 nM, 1 nM to 200 nM or 12 nM to 150 nM.

In another embodiment, when using a fluorophore as the further detection means in the sensor according to the present application, the change in the fluorescence intensity may be measured. Upon binding of the metal ions to the complexing agent to which a fluorophore is attached, the fluorescence intensity may be changed. In the case of $Cu^{2+}$ ions binding to a copper-binding motif as complexing agent, the fluorescence intensity is reduced i.e. quenched. Metal ion concentrations, in particular $Cu^{2+}$ ion concentration in the fluid sample with the sensor according to the present invention can be quantitatively detected in a range from 1 nM to 30 mM, 5 nM to 20 mM, 10 nM to 10 mM, 12 nM to 5 mM, in particular in a range from 1 nM to 60 µM, 5 nM to 40 µM, 10 nM to 10 µM, 12 nM to 5 µM, 1 nM to 500 nM, 1 nM to 200 nM or 12 nM to 150 nM.

The quantitative detection of $Cu^{2+}$ ion concentrations in a fluid sample as low as about 1 nM is very important for application of the sensor in the detection of trace amounts of copper ions in food/water samples or for detection of copper ions in the early diagnosis of AD in urine. A copper value, i.e. amount of $Cu^{2+}$ ions of about 12 µg/day in the 24 h urine of AD patients (J Trace Elem Met Biol 2018, 45, 181-188) and taking into account that 24 h collected urine is around 1.5 to 2.0 L leads to a copper concentration in urine in a range of 100 to 130 nM for AD patients. The sensor according to the present application can be used to measure the copper ($Cu^{2+}$) ion concentration directly from the urine sample in a simple two-step procedure, for example by immersing a test strip with the immobilized sensor in the urine sample or by mixing a solution of the sensor of the present application with the urine sample or by dripping the urine sample onto the sensor of the present application and then subjecting the sample to a fluorescence light source. For individuals with Wilson's disease the concentration of free $Cu^{2+}$ ions in urine ($Cu^{2+}$ ions not bound to ceruloplasmin (non-CP Cu)) is determined to be about 5 to 10 µM, which is even higher than in AD patients. For healthy individuals with a copper value of 4.82 µg/day the $Cu^{2+}$ ion or copper concentration varies between 40 to 50 nM. All $Cu^{2+}$ ion or copper values for healthy individuals and patients of AD and Wilson's disease are within the range of detection of the sensor according to the present application.

A qualitative and/or quantitative detection of metal ions in a fluid sample may also be performed by both measuring the change in the current-voltage characteristics of the sensor and the change in fluorescence intensity.

The sensor according to the present application may be regenerated to be applicable for further detection cycles. Regeneration is conducted by subjecting the sensor to a further complexing agent which may also be termed regeneration complexing agent. The further complexing agent differs from the complexing agent used in the sensor. The complexing agent can be, for example, ethylene diamine tetraacetic acid (EDTA). In a preferred embodiment, the sensor according to the present application can be regenerated at least 6 times.

The sensor of the present application may be manufactured as follows. The complexing agent comprising a peptide comprising 2-6 amino acids, modified amino acids or amino acid mimics may be synthesized following the standard solid phase peptide synthesis (SPPS). In case a fluorophore is used as further detection means, the fluorophore may be attached via standard peptide coupling chemistry to the N-terminus of the peptide complexing agent. The linker moiety may also be attached via standard peptide coupling chemistry to the C-terminus of the peptide. The complexing agent to which optionally a flurorphore is attached may be attached, to or immobilized on the surface of the polymer membrane with nanopores via the linker moiety.

The sensor according to the present application can also be used in combination with a test strip for the detection of metal ions in a fluid sample. The test strip may comprise the sensor according to the present application on a carrier material. The carrier material may have at least two slots or indentions into which a fluid sample may be applied. In one of the slots/indentions the fluid sample to be analyzed for the qualitative and/or quantitative detection of metal ions can be applied. In the further slot/indention a control solution may be applied. In case a quantitative detection of metal ions in the fluid sample should be performed in a further slot/indention a calibration solution may be applied. In a preferred embodiment, the sensor used in combination with a test strip comprises the complexing agent such as a copper-binding motif, a linker moiety and an ion-track etched PET membrane and a fluorophore as detection means.

DESCRIPTION OF FIGURES

FIG. 2(a) shows UV-vis spectra of the $Cu^{2+}$ complex at pH 8 (black line) and $Ni^{2+}$ complex at pH 10.5 (grey line) with the peptide (cf. also FIG. 2e) attached to a linker moiety ($PEG_4$), the insert showing a magnification at 350 to 650 nm. FIG. 2(e) is a scheme of the complex between the copper-binding motifs DAP-βAla-His, DAP-βAla-Asp, DAP-βAla-Ala and the metal $M^{2+}$ ($Cu^{2+}$), wherein R is either 5(6)-carboxyfluorescein (FAM) or acetyl (Ac).

EXAMPLES

Figure 1:
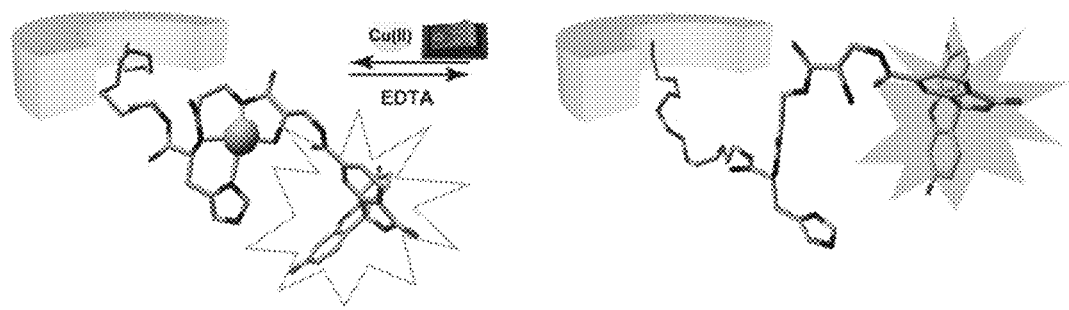
FIG. 1 shows the "on-off" characteristics of a detection method using the sensor of the present application comprising 5(6)-carboxyfluorescein as further detection means.

Solid Phase Peptide Synthesis (SPPS) and Characterization of Copper-Binding Motifs Used as Complexing Agents 5(6)-carboxyfluorescein-DAP-βAla-His-linkerPEG$_4$ (1), Acetyl(Ac)-DAP-βAla-His-linkerPEG$_4$ (2), Acetyl(Ac)-DAP-βAla-Asp-linkerPEG$_4$ (3) and Acetyl(Ac)-DAP-βAla-Ala-linkerPEG$_4$ (4) were synthesized following the standard Fmoc-SPPS using chlorotrityl chloride resin (0.966 mmol/g). After linkerPEG$_4$ coupling the resin was capped with 8.5:1:0.5 dichloromethane (DCM)/methanol/N-ethyl-N-(propan-2-yl)propan-2-amine (DIEA) followed by coupling of Fmoc-His(Trt)-OH, Fmoc-Asp(Trt)-OH or Fmoc-Ala(Trt)-OH, Fmoc-βAla-OH, Fmoc-Dap(Boc) and 5(6)-carboxyfluorescein (fluorophore only for (1)), correspondingly. Deprotection was obtained by 20% piperidine in N,N-dimethylformamide (DMF) and the coupling efficiency was monitored by UV-Vis-spectrometry at 301 nm. Copper-binding motifs (2, 3 and 4) were acetylated at the N-terminus with acetic anhydride. The final cleavage of copper-binding motifs (1) to (4) from the resin was carried out in 2/2/48/48 triisopropylsilane (TIPS)/water/trifluoroacetic acid (TFA)/DCM and agitated for 1 h at room temperature.

RP-HPLC purification was performed on a C18 column (MultoKrom 100-5. 250×20 mm, 100 Å pore diameter, 5.0 μm particle size) using a linear gradient of 5 to 40% of eluent B (eluent A: water (0.1% TFA) and eluent. B: acetonitrile (0.1% TFA)) in 60 min. Copper-binding motifs (2-4) were purified following an isocratic method of 5% eluent B for 12 minutes followed by a linear gradient to 30% eluent B within a total of 60 minutes. The molecular mass was confirmed by ESI-MS ((1): m/z: [M+H]$^+$ calculated for C44H51N7O15 918.92, found 918.35; (2): m/z: [M+H]$^+$ calculated for C25H43N7O10 602.31, found 602.31), (3): m/z: [M+H]$^+$ calculated for C23H41N5O15 580.28, found 580.28: (4): m/z: [M+H]$^+$ calculated for C22H41N5O10 536.26, found 536.29).

Collected fractions were combined, freeze-dried and stored at −28° C. Purity of the collected fractions was confirmed by analytical RP-HPLC on a Waters XC e2695 system (Waters, Milford, MA, USA) employing a Waters PDA 2998 diode array detector equipped with ISAspher 100-3 C18 (C18, 3.0 μm particle size, 100 Å pore size, 50×4.6 mm, Isera GmbH, Duren, Germany). The copper-binding motif (1) was eluted with a gradient of 0%-30% eluent B in 10 min at a flow rate of 2 mL/min. (2), (3) and (4) were eluted using a isocratic method of 0% eluent B for 4 minutes followed by a linear gradient to 30% eluent B in 20 minutes total run time. Chromatograms were extracted at 214 nm. The molecular weight of the purified copper-binding motifs as well as complexation of (1) to (4) with Cu(II), Ni(II) was confirmed by ESI mass spectrometry on a TOF-Q impact II spectrometer (Bruker Daltonik GmbH, Bremen, Germany) and calibrated using Bruker's ESI-Tune-Mix.

Preparation of a Sensor Comprising a Copper-Binding Motif, a Fluorophore, a Linker Moiety and an Ion-Track Etched PET-Membrane with Nanopores Ion-track etched PET-membranes with conical nanopores were fabricated through asymmetric chemical etching of latent ion tracks as has been described in *Nucl Instrum Methods Phys Res, Sect B* 2001, 184, 337-346. PET foils or membranes were first irradiated with single swift heavy ions (Au) of kinetic energy 11.4 MeV/nucleon at the linear accelerator UNILAC (GSI Helmholtz Centre for Heavy Ion Research, Darmstadt, Germany). Then, the latent ion tracks in the polymer foils or membranes were sensitized with soft UV light. The chemical track-etching process was performed in a conductivity cell. The ion tracked foils or membranes were fixed in between two chambers of the cell. An etching solution (9 M NaOH) was filled in one chamber and a stopping solution (1 M KCl+1 M HCOOH) was filled in the other chamber. The etching process was carried out at room temperature. The etching process was monitored by applying a potential of −1 V across the foil or membrane. The etching process was stopped when the current reached a certain defined value after the breakthrough point. Then, the etched foil or membrane was washed with stopping solution and dipped in deionized water overnight to remove residual salts.

The carboxylic acid groups on the polymer foil or membrane surface, in particular on the surface of the nanopores originated from the chemical etching. These groups were first activated through standard carbodiimide coupling chemistry. The track-etched foil or membrane was exposed to an ethanol solution containing 1-ethyl-3-(3-dimethylaminopropyl)carbodiimide (EDC) (100 mM) and pentafluorophenyl (PFP) (200 mM) at room temperature for 1 h. After washing with ethanol several times, the activated polymer foil or membrane was treated with ethylenediamine (EDA, 50 mM) solution overnight. During this reaction period, amine-reactive PFP-esters were covalently coupled with amine group of the EDA. Subsequently, the modified polymer foil or membrane was washed thoroughly with ethanol followed by careful rinsing with deionized water.

Figure 2:
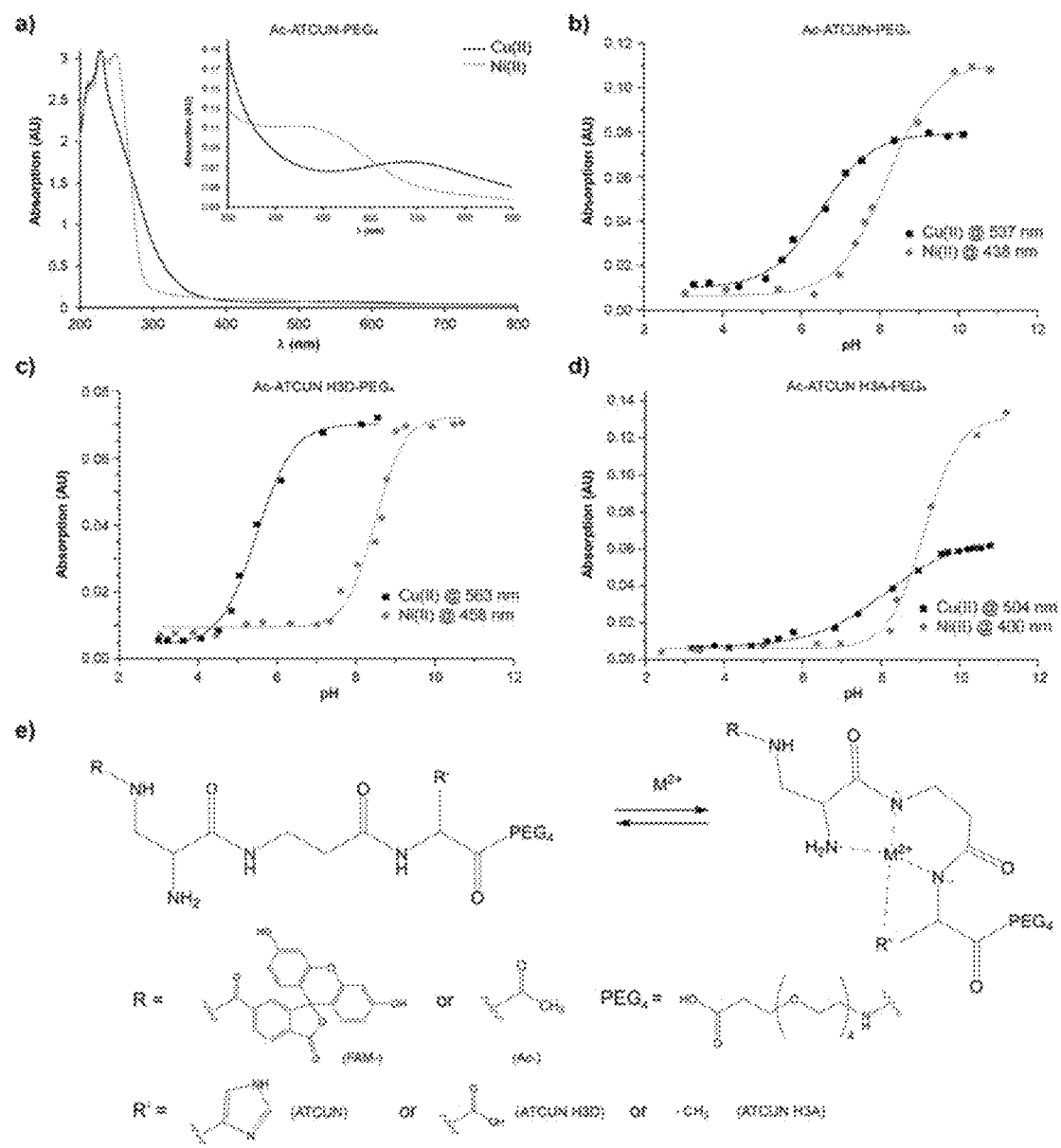
FIGS. 2(b-d) are UV-vis spectra showing the pH dependent formation of the $Cu^{2+}$ complex (black square) in relation to the formation of the corresponding $Ni^{2+}$ complex (grey dots) with the peptides b) Ac-DAP-βAla-His (Ac-ATCUN) (1 mM, water), c) Ac-DAP-βAla-Asp (Ac-ATCUN H3D) (1 mM, water) and d) Ac-DAP-βAla-Ala (Ac-ATCUN H3A) (1 mM, water), attached to a linker moiety ($PEG_4$). Boltzman fit (black and grey lines) show the sigmoidal trend of the complex formation.

Then, the EDA-modified foil was used for the immobilization of the sensor having carboxylic acid groups at the terminus of the linker moiety (FIG. 2(c)). Carboxylic acid groups of the linker were activated with 1-[bis(dimethylamino)methylene]-1H-1-1,2,3-triazolo[4,5]pyridinium-3-oxide hexa-fluorophosphate (HATU)/DIEA and reacted with (1) to (4) (0.5 mM) in DMF, and left to react overnight at room temperature.

Figure 4:
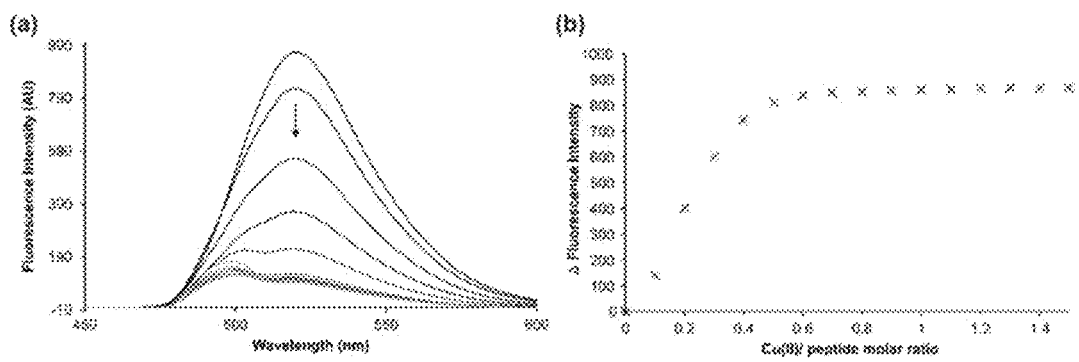
FIG. 4(a) is a fluorescence spectrum showing the decrease of fluorescence intensity of 5(6)-carboxyfluorescein-DAP-βAla-His-linker$PEG_4$ (0.1 µM, phosphate buffer, pH 8.0) upon addition of $CuCl_2$ from 0 to 0.15 µM in water.
FIG. 4(b) shows the change in fluorescence intensity as a function of the molar ratio of $Cu^{2+}$ to 5(6)-carboxyfluorescein-DAP-βAla-His-linker$PEG_4$ (termed "peptide" in the description of the x-axis).
Figure 5:
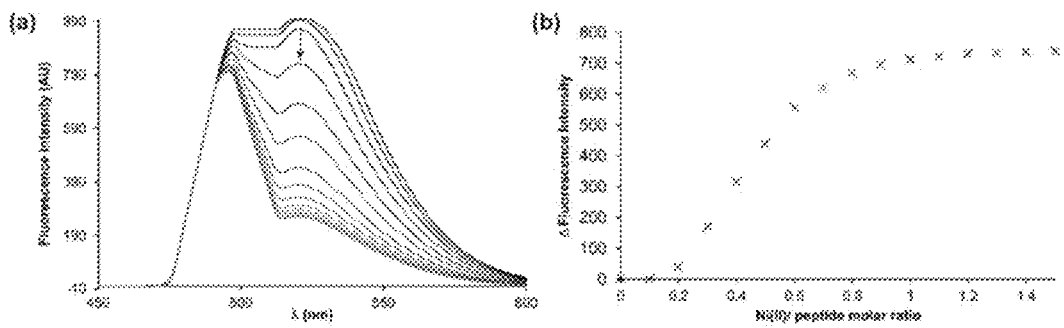
FIG. 5(a) is a fluorescence spectrum showing the decrease of fluorescence intensity of 5(6)-carboxyfluorescein-DAP-δAla-His-linker$PEG_4$ (0.025 µM, CAPS buffer, pH 10.55) upon addition of $Ni^{2+}$ from 0 to 0.038 µM in water.
FIG. 5(b) shows the change in fluorescence intensity as a function of the molar ratio of $Ni^{2+}$ to 5(6)-carboxyfluorescein-DAP-βAla-His-linker$PEG_4$ (termed "peptide" in the description of the x-axis).

Characterization of the $Cu^{2+}$ and $Ni^{2+}$ Complex with the Copper-Binding Motif as Complexing Agent of the Sensor and Selectivity of the Sensor of the Present Application for $Cu^{2+}$ Ions Over $Ni^{2+}$ and $Zn^{2+}$ Ions Fluorescence studies performed with (1) at pH 8.0 at which pH optimal formation of the Cu-complex was observed, show that when adding one equivalent of $Cu^{2+}$ ions, fluorescence intensity is quenched to 89% (11% remained intensity) by formation of a non-fluorescent complex between the $Cu^{2+}$ ions and the copper binding motif (FIGS. 4(a),(b)). For $Ni^{2+}$ ions pH 10.55 was evaluated as the lowest pH at which complete formation of the Ni-complex was achieved, and upon addition of 1 equivalent $Ni^{2+}$ ions a remaining fluorescence of 29% is observed (FIGS. 5(a),(b)). To obtain a distinguished selectivity of the sensor towards $Cu^{2+}$ ions, a pH of 6.50 was determined for copper-binding motif DAP-βAla-His. This can be seen in the pH titration study shown in FIG. 2(b). A similar selectivity towards $Cu^{2+}$ ions at pH 6.5 can be achieved with DAP-βAla-Asp (Ac-ATCUN H3D) (FIG. 2(c)) and with DAP-βAla-Ala (Ac-ATCUN H3A) (FIG. 2(d)). Moreover, Ac-ATCUN H3D has an even broader pH range (approx. pH 5.5 to 7.2) in which it is highly selective for $Cu^{2+}$ (FIG. 2(c)). pH Titration studies were performed using a 1 mM sensor solution in deionized water. One equivalent of the according metal ion, $Cu^{2+}$ or $Ni^{2+}$, was added and the pH lowered to pH <3 using 0.1 mM HCl. Adding small aliquots of 0.1 mM NaOH the pH was increased and with each step a spectrum recorded.

Figure 6:
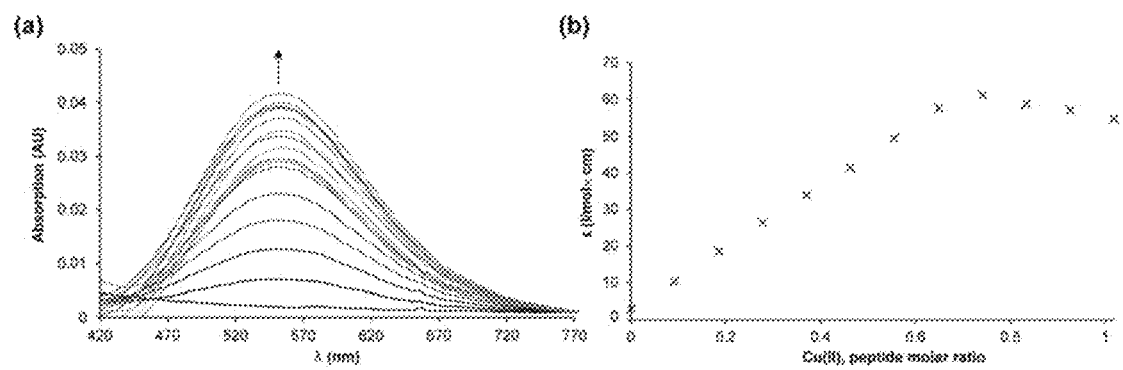
FIG. 6(a) is an UV-Vis titration spectrum of Ac-DAP-βAla-His-linker$PEG_4$ (0.68 mM, MES buffer pH 6.50) upon addition of $Cu^{2+}$ (0 to 0.7 mM) in water.
FIG. 6(b) shows the absorption coefficient ε of the $Cu^{2+}$ complex as a function of the molar ratio of $Cu^{2+}$ to Ac-DAP-βAla-His-linkerPEG$_4$ (termed "peptide" in the description of the x-axis).

At pH of 6.50 nickel ion complexation is insignificant whereas for copper this pH represents the $pH_{50}$. UV-Vis titration using different $Cu^{2+}$ ion concentrations shows the anticipated behavior at $pH_{50}$ illustrating a saturation after addition of around 0.5 equivalents $Cu^{2+}$ ions (FIGS. 6(a), (b)).

Figure 3:
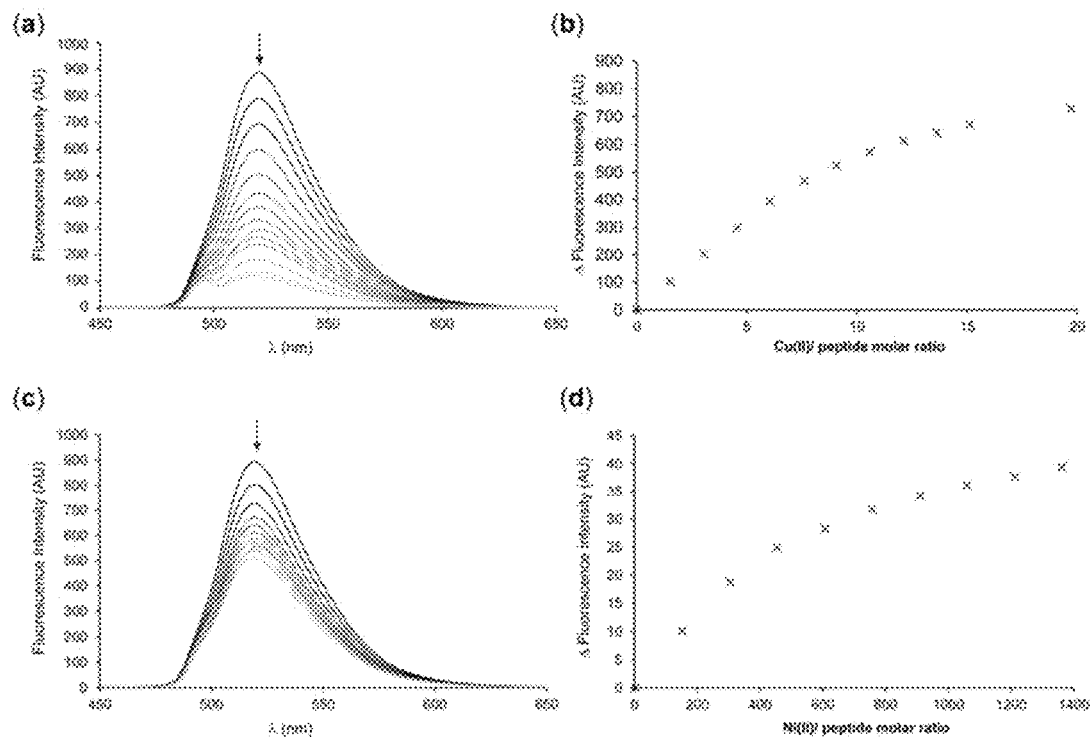
FIG. 3(a) is a fluorescence spectrum showing the decrease of fluorescence intensity of 5(6)-carboxyfluorescein-DAP-βAla-His-linker$PEG_4$ (1 µM, 2-(N-morpholino)ethanesulfonic acid (MES) buffer, pH 6.50) upon addition of $CuSO_4$ from 0 to 25 µM in water.
FIG. 3(b) shows the change in fluorescence intensity as a function of the molar ratio of $Cu^{2+}$ to 5(6)-carboxyfluorescein-DAP-βAla-His-linker-$PEG_4$ (termed "peptide" in the description of the x-axis).
FIG. 3(c) is a fluorescence spectrum showing the decrease of fluorescence intensity of 5(6)-carboxyfluorescein-DAP-βAla-His-linker$PEG_4$ (1 µM, MES buffer, pH 6.50) upon addition of $NiSO_4$ from 0 to 3 mM in water.
FIG. 3(d) shows the change in fluorescence intensity as a function of the molar ratio of $Ni^{2+}$ to 5(6)-carboxyfluorescein-DAP-βAla-His-linker$PEG_4$ (termed "peptide" in the description of the x-axis).

The fluorescence spectrum in FIG. 3(a) shows the decrease of fluorescence intensity of 5(6)-carboxyfluorescein-DAP-βAla-His-linkerPEG$_4$ (1) (1 μM, MES buffer, pH 6.50) upon addition of CuSO$_4$ from 0 to 25 μM. Emission (A) was determined to be 518 nm. Fluorescence titration upon addition of 20 equivalents of $Cu^{2+}$ at pH 6.50 showed quenching of the fluorescence intensity to 88% (12% remaining fluorescence intensity) (FIG. 3(b)). In comparison thereto, fluorescence titration upon addition of nickel at pH 6.50 showed quenching of the fluorescence intensity after addition of 1364 equivalents of nickel to only 43% (57% remaining fluorescence intensity) (FIGS. 3(c),(d)) which can be explained by the insufficient formation of the nickel complex at pH 6.50.

Figure 7:
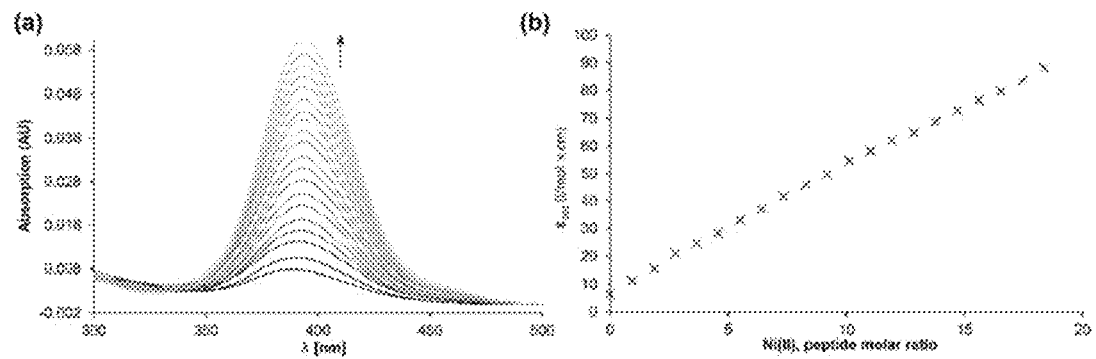
FIG. 7(a) is an UV-Vis titration spectrum of Ac-DAP-βAla-His-linkerPEG$_4$ (0.68 mM, MES buffer pH 6.50) upon addition of NiSO$_4$ (0 to 16 mM) in water.
FIG. 7(b) shows the change in absorption as a function of the molar ratio of $Ni^{2+}$ to Ac-DAP-βAla-His-linkerPEG$_4$ (termed "peptide" in the description of the x-axis).

Further, an experiment with $Ni^{2+}$ and Ac-DAP-βAla-His-linkerPEG$_4$ (2) at a pH of 6.50 did not show the required maximum absorption at 438 nm which indicates the formation of the planar coordination of $Ni^{2+}$ to the complexing agent, i.e. the copper-binding motif, but rather showed a maximum absorption at 394 nm indicating that the complex between the copper-binding motif and the $Ni^{2+}$ ions is not assembled but rather a non-specific octahedral binding is achieved (FIGS. 7(a),(b)). Thus, it was confirmed that when adjusting the pH to the claimed range, a selectivity of the sensor according to the present application is guaranteed for $Cu^{2+}$ over $Ni^{2+}$ and the almost exclusive formation of the copper-binding complex is confirmed. This also applies to (3) and (4).

Figure 8:
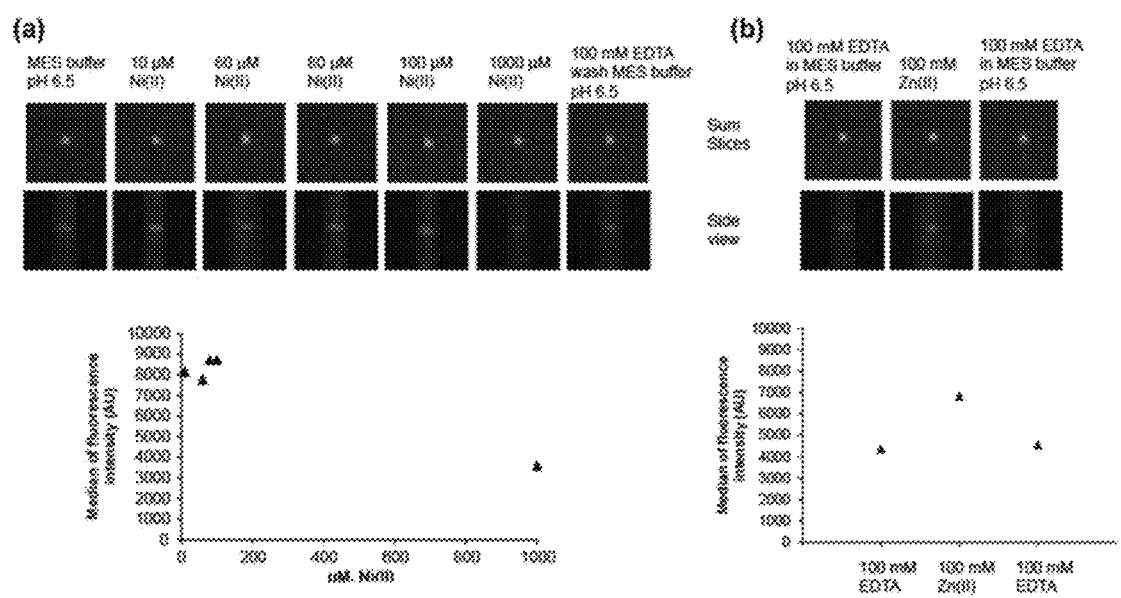
FIG. 8(a) shows fluorescence emission images obtained with confocal laser scanning microscopy (CLSM) after addition of different amounts of NiSO$_4$ (top). It also shows the median of fluorescence intensity in relation to different amounts of NiSO$_4$ (bottom).
FIG. 8(b) shows a fluorescence image obtained with CLSM after addition of 100 mM ZnSO$_4$ (top). It also shows the median of fluorescence intensity after addition of 100 mM ZnSO$_4$ in relation to reference "washed out" nanopores fluorescence intensities with 100 mM EDTA (bottom).

In FIG. 8(a) it is demonstrated that there is no decrease in fluorescence intensity visible for $Ni^{2+}$ ions in a range of 0 to 200 μM in MES buffer, pH 6.50. Only upon addition of 1 mM (1000 μM) NiSO$_4$ in MES buffer a reduction in fluorescence intensity is observed. With regard to Zn (FIG. 8(b)) it can be seen that even addition of 100 mM ZnSO$_4$ in MES buffer, pH 6.50 does not affect the fluorescence intensity. The titration experiments were performed at pH 6.50 to demonstrate selectivity towards $Cu^{2+}$ ions.

The binding constants for and $Ni^{2+}$ to the complexing agent, i.e. the copper-binding motif according to the present application were determined by UV-Vis spectroscopy at pH 6.50 using the Benesi-Hildebrand method. The obtained binding constants were similar to the binding constants determined with fluorescence spectroscopy using the Stern-Volmer plot at pH 6.50. Binding constants are as follows log $K_{Cu}$=6.8 for 5(6)-carboxyfluorescein-DAP-βAla-His-linkerPEG$_4$ (1) with $K_b$=6.27×10$^6$ M$^{-1}$ and log $K_{Cu}$=6.56 for Ac-DAP-βAla-His-linkerPEG$_4$ (2) with $K_b$=4.00×10$^6$ M$^{-1}$ showing a slightly better binding to the moiety comprising the fluorophore. At pH 6.50 the binding constants towards nickel were determined to be log $K_{Ni}$=3.26 with $K_b$=1.80× 10$^3$ M$^{-1}$ for (1) and log $K_{Ni}$=2.76 with with $K_b$=5.80×10$^2$ M$^{-1}$ for (2) demonstrating again the outstanding selectivity towards copper. By optimizing the pH value a superior copper binding of the copper-binding motif comprised by the sensor of the present application was achieved, leading to a selective formation of the Cu-complex at the respective pH value.

Figure 9:
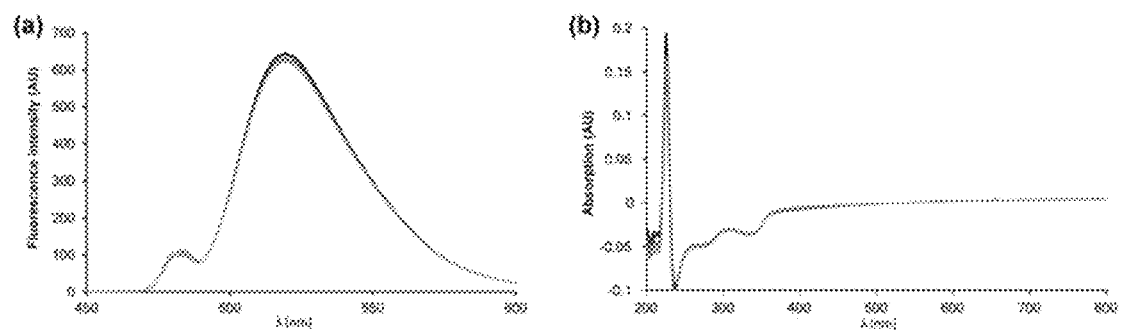
FIG. 9(a) is a fluorescence spectrum showing fluorescence titration results of 5(6)-carboxyfluorescein-DAP-βAla-His-linkerPEG$_4$ (1 μM, 100 mM MES buffer, pH 6.50) upon addition of ZnSO$_4$ from 0 to 3 mM in water.
FIG. 9(b) shows an UV-vis titration spectrum of Ac-DAP-βAla-His-linkerPEG$_4$ (1 mM, 100 mM MES buffer pH 6.50) upon addition of ZnSO$_4$ (0 to 2 mM) in water.

No binding of Zn$^{2+}$ ions was detected for 5(6)-carboxyfluorescein-DAP-βAla-His-linkerPEG$_4$ (1) or Ac-DAP-βAla-His-linkerPEG$_4$ (2) (FIGS. 9(a),(b)).

Measurement of Fluorescence Intensity of the Sensor Comprising a Copper-Binding Motif, 5(6)-Carboxyfluorescein as Detection Means, a Linker Moiety and an Ion-Track Etched PET-Membrane with Nanopores When using fluorescence intensity as parameter for determining the presence and/or concentration of Cu$^{2+}$ ions, in particular when using 5(6)-carboxyfluorescein as fluorophore a decrease in fluorescence intensity indicates the presence of Cu$^{2+}$ ions. The higher the Cu$^{2+}$ concentration the lower the fluorescence intensity. This has been shown in FIGS. 10(a)-(d). FIGS. 10(a)-(d) show 5(6)-carboxyfluorescein-DAP-βAla-His-linkerPEG$_4$ (1) attached to an ion-track etched PET-membrane with nanopores (via the linker moiety linkerPEG$_4$) which was subjected to confocal laser scanning microscopy (CLSM) measurements.

Figure 10:
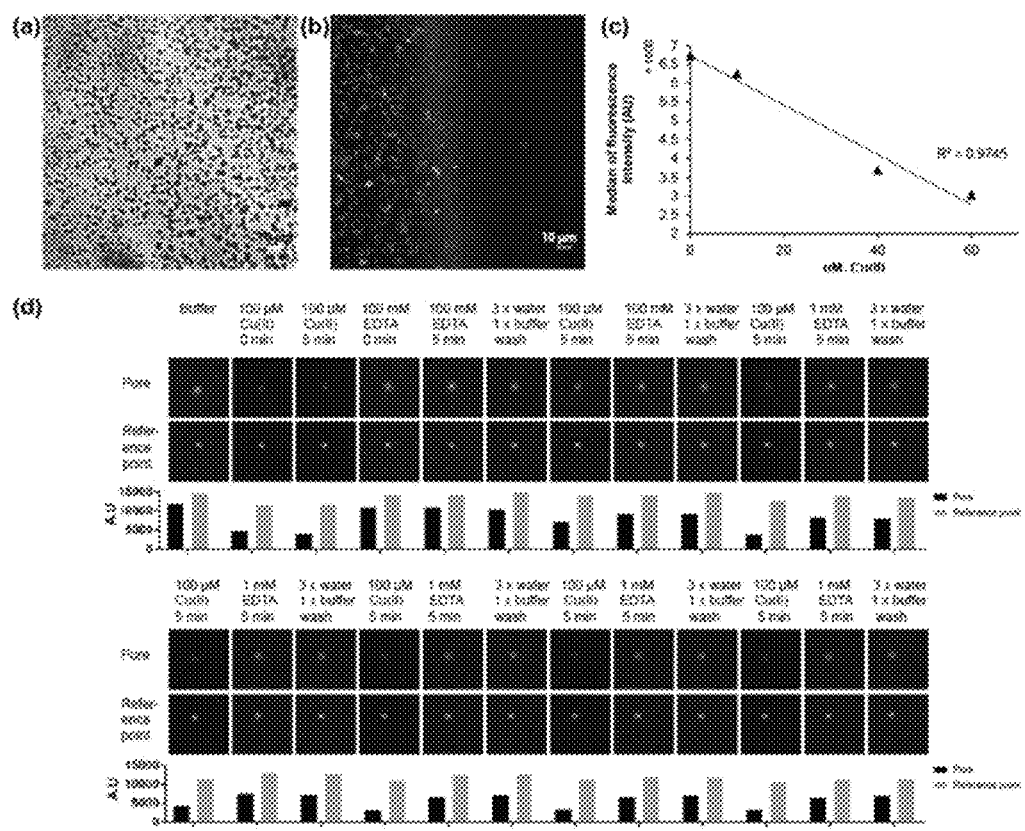
FIG. 10(a) shows the surface of an ion-track etched PET-membrane with nanopores upon which 5(6)-carboxyfluorescein-DAP-βAla-His-linkerPEG$_4$ was immobilized (via linkerPEG$_4$ as the linker moiety) (reflected light).
FIG. 10(b) shows confocal laser scanning microscopy (CLSM) images of a sensor comprising 5(6)-carboxyfluorescein-DAP-βAla-His-linkerPEG$_4$ linked (via linkerPEG$_4$) to an ion-track etched PET-membrane with nanopores. The area on the right hand side represents nanopores which have not been etched and thus no 5(6)-carboxyfluorescein-DAP-βAla-His-linkerPEG$_4$ was immobilized thereon.
FIG. 10(c) shows the linear dependency of decrease in median fluorescence intensity with increase in $Cu^{2+}$ ion concentration.
FIG. 10(d) shows CLSM fluorescence emission images of the "on-off" characteristics the sensor, in particular the re-usability of the sensor after regeneration with 1 mM EDTA and washing with water and MES buffer, pH 6.50.

5(6)-carboxyfluorescein-DAP-βAla-His-linkerPEG$_4$ (1) is almost exclusively present on the surface of the nanopores of the ion-track etched PET-membrane or foil as can be seen in FIG. 10(a) and displays a green color when excited by the laser at 488 nm in the CLSM image (FIG. 10(b)). FIG. 10(d) shows a titration experiment showing the dependency of decrease in fluorescence with the increase in Cu$^{2+}$ ion concentration as well as the re-usability of the sensor of the present application. CuSO$_4$ was added in concentrations from 0 to 100 µM in MES buffer solution, pH 6.50. In particular, the "on-off" characteristics of the sensor of the present application showing re-usability after regeneration with 1 mM EDTA and washing with water and MES buffer, pH 6.50 can be seen in said figure. FIG. 10(c) shows clearly the linear dependency of decrease in fluorescence with the increase in Cu$^{2+}$ ion concentration. This experiment was performed by measuring the decrease in median fluorescence intensity after addition of CuSO$_4$ from 0 to 60 µM in MES buffer, pH 6.5.

As can be seen in FIGS. 10(c) and (d) fluorescence intensity decreases with addition of Cu$^{2+}$ with a linear dependency. Furthermore, when EDTA was used as complexing agent it was possible to regenerate the Cu$^{2+}$ sensitivity of the sensor. As can be seen in FIG. 10(d) the sensing towards Cu$^{2+}$ could be revived for at least seven times. Further, a shelf life of the sensor of at least six months was confirmed.

Also the limit of detection (LOD) for Cu$^{2+}$ ions using the fluorescence signal was determined. In order to determine the sensitivity of the sensor according to the present application the limit of detection of the sensor comprising 5(6)-carboxyfluorescein-DAP-βAla-His-linkerPEG$_4$ (1) towards Cu$^{2+}$ ions in solution from fluorescence intensity titration studies is defined to be 12 nM. This value is extremely important for application of the sensor according to the present invention for detection of trace amounts of copper ions in food/water control or detection of copper ions for the early diagnosis of Alzheimer's disease in urine.

Figure 11:
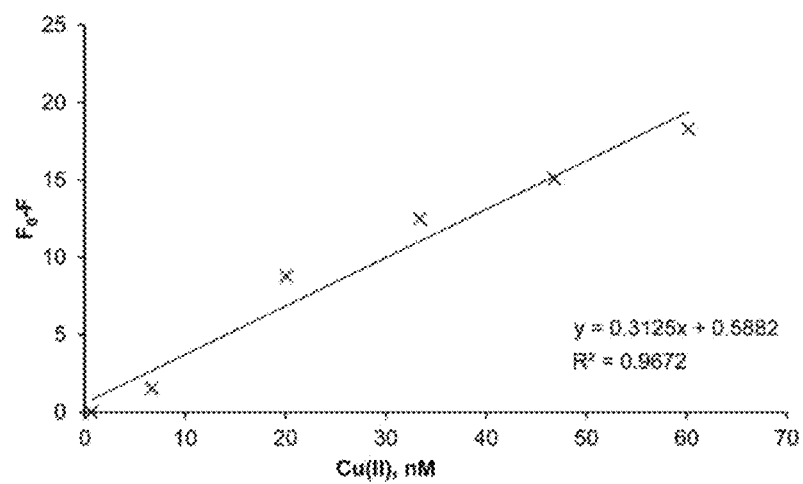
FIG. 11 shows a plot of $F_0$–F in relation to $Cu^{2+}$ ion concentration for determining the limit of detection (LOD) of the sensor comprising 5(6)-carboxyfluorescein-DAP-βAla-His-linkerPEG$_4$ (1 μM, 100 mM MES buffer pH 6.50; addition of CuSO$_4$ (0 to 60 nM) in water), wherein $F_0$ is the fluorescence intensity of the solution without analyte, i.e. without $Cu^{2+}$ ions and F is the fluorescence intensity of the solution with $Cu^{2+}$ ions.

The LOD was calculated using the following equation: LOD=(3×σ) slope, wherein σ=standard deviation of blank solution. 1 µL of a blank solution (100 mM MES buffer pH 6.50) was pipetted to a 1 µM peptide solution in 100 mM MES buffer and the difference between fluorescence intensity $F_0$–F relating to the starting intensity was determined (FIG. 11). From a six fold titration study the standard deviation of the change in fluorescence intensity with the addition of blank solution is determined and used as the a value (1.28) (*Eur J Biochem* 2002, 269, 1323-1331)

Figure 12:
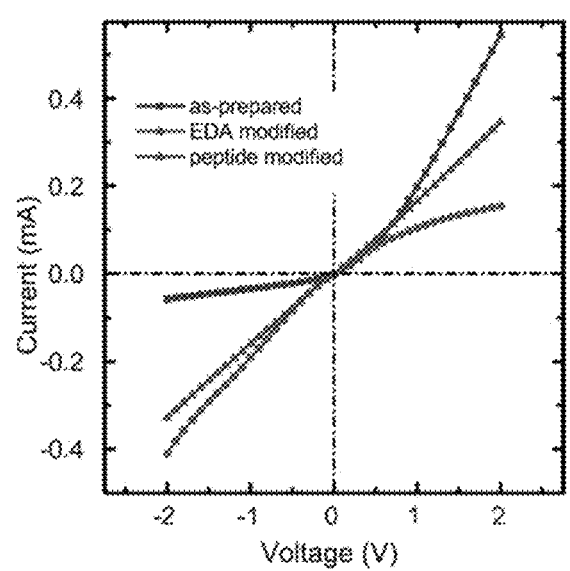
FIG. 12 shows the current-voltage (I-V) characteristics of the ion-track etched PET-membrane with nanopores without any sensor immobilized thereon (as-prepared), the ion-track etched PET-membrane with nanopores modified with EDA (EDA modified) and the ion-track etched PET-membrane with nanopores to which 5(6)-carboxyfluorescein-DAP-βAla-His-linkerPEG$_4$ was immobilized (peptide modified).

Measurement of the Current-Voltage (I-V) Characteristics of the Sensor Comprising a Copper-Binding Motif, a Fluorophore, a Linker Moiety and an Ion-Track Etched PET-Membrane with Nanopores as Detection Means In the following the measurement of the current-voltage (I-V) characteristics of the sensor according to the present application is outlined. The sensor comprises a copper-binding motif, a fluorophore and a linker moiety, i.e. 5(6)-carboxyfluorescein-DAP-βAla-His-linkerPEG$_4$ whereby the copper-binding motif with the fluorophore is attached to the ion-track etched PET-membrane with nanopores by means of the linker. The PET-membrane with nanopores behaves as an ohmic resistor before Cu$^{2+}$ complexation meaning that the net surface charge on the nanopore surface is zero and no flux from the narrow cone opening to the wide opening takes place. The ion-track etched PET-membrane with conical nanopores having carboxyl groups on the surface with no immobilized copper-binding motif (as-prepared) shows a flux from the narrow cone opening to the wide opening because of the negative carboxyl groups (FIG. 12). After modification with ethylene diamine (EDA) the surface charge switches from negative to positive resulting in an anion selectivity and the concomitant inversion of the rectification behavior of the nanopore (EDA modified). Immobilization of the copper-binding motif with the fluorophore via the linker to the surface of the nanopores of the ion-track etched PET-membrane results in change of the nanopore transport behavior from a rectifying to a non-rectifying due to the loss of nanopore surface charges. The PET-membrane with the immobilized copper-binding motif behaves as an ohmic resistor, i.e. the net surface charge on the nanopore walls is zero.

Figure 13:
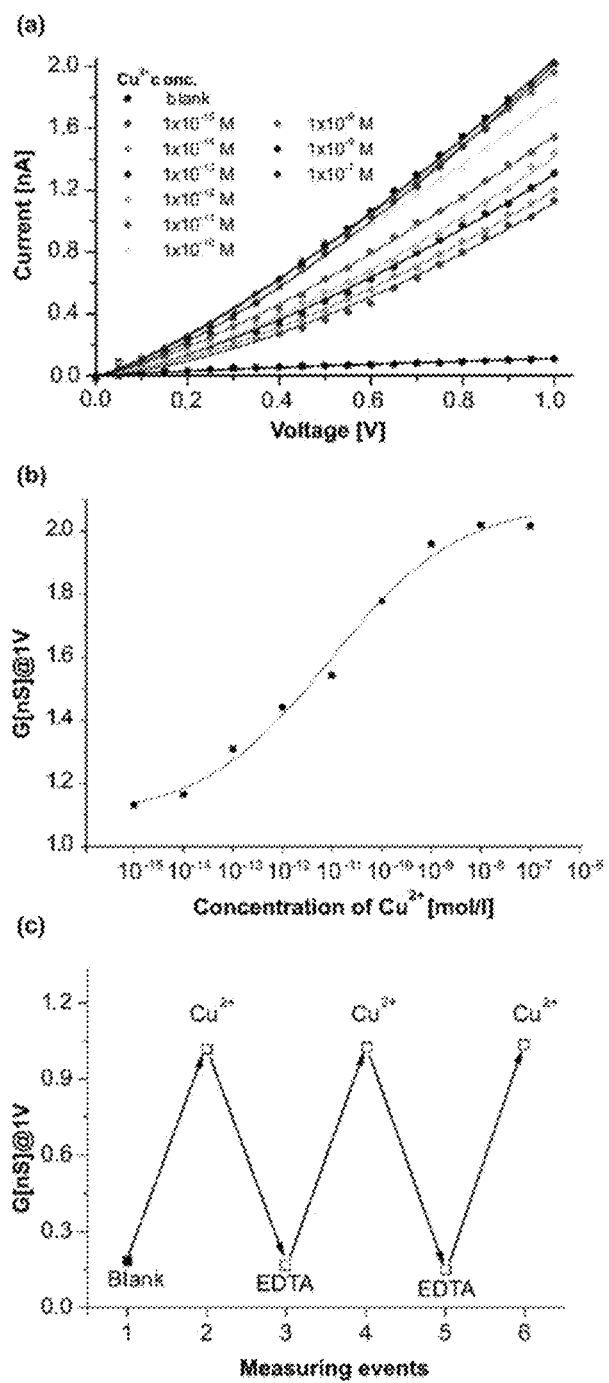
FIG. 13(a) shows the current-voltage (I-V) characteristics of the sensor comprising the ion-track etched PET-membrane with nanopores to which 5(6)-carboxyfluorescein-DAP-βAla-His-linkerPEG$_4$ was immobilized upon application of different concentrations of $Cu^{2+}$ ions.
FIG. 13(b) shows the conductance depending on the $Cu^{2+}$ ion concentration.
FIG. 13(c) shows the reversible complexation/decomplexation behavior of $Cu^{2+}$ ions when using EDTA as the further complexing agent.
Figure 14:
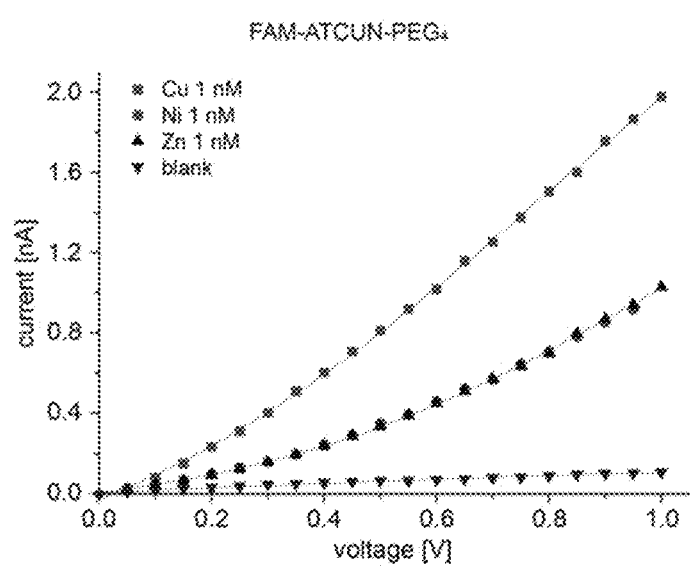
FIG. 14 shows the current-voltage (I-V) characteristics of the sensor comprising the ion-track etched PET-membrane with nanopores to which 5(6)-carboxyfluorescein-DAP-βAla-His-linkerPEG$_4$ was immobilized upon application of 1 nM concentration of $Cu^{2+}$, $Ni^{2+}$ and $Zn^{2+}$ ions, in buffer (MES/KCl 100 mM, pH 6.5).

Upon complexation of Cu$^{2+}$ by the copper-binding motif, a positive charge is generated on the nanopore surface, which concomitantly changes the ion transport behavior of the nanopore. The nanopore becomes ion selective as evidenced from the successive increase in positive current by increasing the Cu$^{2+}$ concentration ranging from fM to nM concentrations as shown in FIGS. 13(a) and (b). Thus, the presence of the generated Cu complex on the surface of the nanopores switches the nanopore transport behavior from a non-conducting "off" state to a conducting "on" state. As can be further seen in FIGS. 13(a) and (b) the sensor according to the present application is able to recognize Cu$^{2+}$ ions even at concentrations as low as 1 fM and this recognition process can be transduced in an electronic signal originating from the transport behavior of the nanopore. From the data given in FIG. 13 it can be seen that the sensor exhibits a remarkable interaction ability towards Cu$^{2+}$ due to the particular copper-binding motif used in the sensor according to the present application. Further, the ion selectivity of the sensor (PET immobilized FAM-ATCUN-PEG$_4$, cf. FIG. 2e) for different metal ions such as Cu, Ni and Zn at pH 6.5 is shown in FIG. 14 clearly demonstrating a strong Cu selectivity.

The reproducibility of the conductance measurements over at least six cycles is shown in FIG. 13(c).

The present application further elate to the following items.

Item 1. A sensor for detection and/or concentration determination of Cu$^{2+}$ ions in a fluid according to the invention, wherein the complexing agent is the copper-binding motif 2,3-diaminopropionic acid(DAP)-βAla-X, wherein X is an amino acid or a modified amino acid, in particular wherein X is histidine (His), alanine (Ala) or aspartic acid (Asp).

Item 2. The sensor according to item 1 comprising the copper-binding motif 2,3-diaminopropionic acid(DAP)-βAla-His, DAP-βAla-Asp, or DAP-βAla-Ala, wherein DAP is preferably L-DAP.

Item 3. The sensor according to items 1 and 2, wherein the detection means further comprises a fluorophore, in particular 5(6)-carboxyfluorescein or 6-carboxyfluorescein.

Item 4. The sensor according to item 3, wherein the fluorophore is attached to the N-terminus of the DAP.

Item 5. The sensor according to items 1 to 4 wherein the linker moiety is attached to the C-terminus of the X.

Item 6. The sensor according to any one of items 1 to 5, wherein the ion-track etched PET membrane with nanopores is a membrane with functional groups such as carboxylate and/or amino groups on the surface of the membrane and on the surface of the nanopores.

Item 7. The sensor according to any one of items 1 to 6, wherein the copper-binding motif to which a fluorophore is attached, is bound via the linker moiety to the surface of the ion-track etched polymer membrane and to the surface of the nanopores thereof.

Item 8. The sensor according to any one of items 1 to 7, wherein the linker moiety comprises polyethylene glycol, in particular wherein the linker moiety has the formula $R_1$—[$CH_2CH_2O$]$_a$—$R_2$, wherein a is preferably 4, $R_1$ is preferably —NH and/or $R_2$ is preferably COO(H)—, wherein a linker moiety having the structure —HN—[$CH_2CH_2O$]$_4$—$CH_2CH_2COOH$ (linkerPEG$_4$) or —HN—[$CH_2CH_2O$]$_4$—$CH_2CH_2COO^-$ is most preferred.

Item 9. The sensor according to any one of items 1 to 8 for selectively detecting Cu$^{2+}$ ions in a fluid in the presence of Ni$^{2+}$ ions and/or Zn$^{2+}$ ions.

Item 10. The sensor according to any one of items 1 to 9 for use in the diagnosis and/or monitoring of diseases, preferably of diseases linked to abnormal Cu$^{2+}$ ion concentrations and/or dysregulated Cu$^{2+}$ ion metabolism, in particular Alzheimer's disease, Wilson's disease and Menke's disease.

Item 11. The sensor according to any one of items 1 to 9 for use in determining Cu$^{2+}$ ion concentration ex vivo in the urine of individuals to diagnose and/or monitor diseases linked to abnormal Cu$^{2+}$ ion concentrations and/or dysregulated Cu$^{2+}$ ion metabolism, in particular Alzheimer's disease, Wilson's disease and Menke's disease.

Item 12. The sensor according to any one of items 10 or 11 for use, wherein an abnormal Cu$^{2+}$ ion concentration relates to a Cu$^{2+}$ ion concentration in a body fluid such as urine and/or serum which is higher or lower than in a healthy individual.

Item 13. The sensor according to any one of items 1 to 9 for use in detecting Cu$^{2+}$ ions and/or determining Cu$^{2+}$ ion concentration in food products or fluids, in particular in environmental water samples.

Item 14. A method for detection of Cu$^{2+}$ ions and/or for determining Cu$^{2+}$ ion concentration in a fluid sample comprising the steps of
  adjusting the pH of a fluid sample to be analyzed to 5.0 to 8.5, in particular to a pH of 6.3 to 7.0.
  contacting the sensor according to any one of items 1-9 with the fluid sample, and
  determining the presence and/or concentration of Cu$^{2+}$ ions in the fluid sample by measuring a change in the parameter of the detection means, and
  optionally further comprising a step of regenerating the sensor by subjecting the sensor to a further complexing agent.

Item 15. The method according to item 14, wherein the further complexing agent comprises EDTA.

Item 16. The method according to item 14, wherein the change in fluorescence intensity is measured, and/or wherein the Cu$^{2+}$ ion concentration in the fluid sample is in a range of 1 nM to 60 µM, in particular in a range of 1 nM to 200 nM.

Item 17. The method according to item 14, wherein the change in the current-voltage characteristics is measured, and/or wherein the Cu$^{2+}$ ion concentration in the fluid sample is in a range of 1 fM to 60 µM, in particular in a range of 1 fM to 200 nM.

Item 18. Test strip for the detection of Cu$^{2+}$ ions in a fluid sample comprising the sensor according to any one of items 1 to 9.

Item 19. A method for manufacturing the sensor according to items 1 to 9 comprising the steps of
  synthesizing a compound including the complexing agent, the linker moiety and a fluorophore by solid phase peptide synthesis,
  providing a polymer membrane, foil or sheet, and
  coupling the compound via the linker moiety to the surface of the polymer membrane.

The invention claimed is:

1. A sensor for detection and/or concentration determination of metal ions in a fluid comprising a complexing agent suitable for binding the metal ions to be detected, detection means and a linker moiety, wherein the detection means comprises a polymer membrane with nanopores.

2. The sensor according to claim 1, wherein the polymer membrane with nanopores is an ion-track etched polymer membrane.

3. The sensor according to claim 2, wherein the ion-track etched polymer membrane is an ion-track etched polyethylene terephthalate (PET) membrane.

4. The sensor according to claim 1, wherein the linker moiety comprises polyethylene glycol.

5. The sensor according to claim 4, wherein the linker moiety has the formula $R_1$-[$CH_2CH_2O$]$_a$—$R_2$, wherein a is from 2 to 10, $R_1$ is —NH and $R_2$ is $CH_2CH_2COO$—.

6. The sensor according to claim 1, wherein the linker moiety is bound to the polymer membrane with nanopores and to the complexing agent suitable for binding the metal ions to be detected.

7. The sensor according to claim 1, wherein the detection means further comprises a fluorophore.

8. The sensor according to claim 7, wherein the fluorophore is 5(6)-carboxyfluorescein.

9. The sensor according to claim 7, wherein the fluorophore is attached to the complexing agent suitable for binding the metal ions to be detected.

10. The sensor according to claim 1, wherein the complexing agent suitable for binding the metal ions to be detected is a peptide comprising 2 to 6 amino acids, modified amino acids, and/or amino acid mimics.

11. The sensor according to claim 1, wherein the sensor selectively detects $Cu^{2+}$ ions in a fluid and/or determines a concentration of $Cu^{2+}$ ions in a fluid.

12. The sensor according to claim 11, wherein the complexing agent suitable for binding $Cu^{2+}$ ions comprises a copper-binding motif.

13. The sensor according to claim 12, wherein the copper-binding motif comprises 2,3-diaminopropionic acid(DAP)-βAla-X, wherein X is an amino acid or a modified amino acid.

14. The sensor according to claim 13, wherein X is histidine (His), alanine (Ala) or aspartic acid (Asp).

15. The sensor according to claim 1, wherein the sensor is used in diagnosing and/or monitoring diseases or for use in detecting metal ions and/or determining metal ion concentration in food products and in environmental water samples.

16. The sensor according to claim 15, wherein the sensor is used in monitoring diseases linked to abnormal $Cu^{2+}$ ion concentrations and/or dysregulated $Cu^{2+}$ ion metabolism.

17. The sensor according to claim 15, wherein the sensor is used in monitoring Alzheimer's disease, Wilson's disease, or Menke's disease.

18. A method for detecting metal ions and/or determining metal ion concentration in a fluid sample comprising the steps of bringing the sensor according to claim 1 into contact with the fluid sample, and determining a presence and/or concentration of metal ions in the fluid sample by measuring a change in current-voltage characteristics of the sensor and/or by measuring a change in fluorescence intensity of the sensor, and optionally further comprising a step of regenerating the sensor by subjecting the sensor to a further complexing agent.

19. The method according to claim 18, wherein the method is used for detection of $Cu^{2+}$ ions and/or for determining $Cu^{2+}$ ion concentration in a fluid sample, wherein the method further comprises the step of adjusting a pH of a fluid sample to be analyzed to 5.0 to 8.5 prior bringing the sensor into contact with the fluid sample.

20. The method according to claim 18, wherein the change in the current-voltage characteristics is measured, and/or wherein the metal ion concentration in the fluid sample is in a range of 1 fM to 60 μM.

21. The method according to claim 18, wherein the change in fluorescence intensity is measured, and/or wherein the metal ion concentration in the fluid sample is in a range of 1 nM to 60 μM.

22. A test strip for detecting metal ions and/or determining a concentration of metal ions in a fluid sample comprising the sensor according to claim 1.

* * * * *